United States Patent [19]

Liberti et al.

[11] Patent Number: 5,622,831

[45] Date of Patent: Apr. 22, 1997

[54] METHODS AND DEVICES FOR MANIPULATION OF MAGNETICALLY COLLECTED MATERIAL

[75] Inventors: Paul A. Liberti, Huntingdon Valley; Yozhou Wang, Media, both of Pa.

[73] Assignee: Immunivest Corporation, Wilmington, Del.

[21] Appl. No.: 482,652

[22] Filed: Jun. 7, 1995

Related U.S. Application Data

[63] Continuation-in-part of Ser. No. 228,818, Apr. 18, 1994, Pat. No. 5,541,072, and Ser. No. 424,271, Apr. 24, 1995, which is a continuation-in-part of Ser. No. 976,476, Nov. 16, 1992, abandoned, which is a continuation-in-part of Ser. No. 588,662, Sep. 26, 1990, Pat. No. 5,200,084.

[51] Int. Cl.⁶ .................... G01N 33/567; G01N 33/553
[52] U.S. Cl. .................. 435/7.21; 435/5; 435/6; 435/7.32; 435/7.94; 436/526; 436/52; 436/806; 436/807; 436/824; 422/50; 210/222; 210/695
[58] Field of Search .................. 435/5, 6, 7.21, 435/7.32, 7.92, 7.94; 436/526, 806, 807, 824, 43, 52; 422/50, 68.1; 209/213, 214; 210/222, 695, 767

[56] References Cited

U.S. PATENT DOCUMENTS

| | | | |
|---|---|---|---|
| 3,228,878 | 1/1966 | Moody | 210/695 |
| 3,326,374 | 6/1967 | Jones | 209/214 |
| 3,608,718 | 9/1971 | Aubrey et al. | 209/214 |
| 3,676,337 | 7/1972 | Kolm | 210/695 |
| 3,902,994 | 9/1975 | Maxwell et al. | 209/213 |
| 3,970,518 | 7/1976 | Giaever | 435/239 |
| 4,018,886 | 4/1977 | Giaever | 436/526 |
| 4,069,145 | 1/1978 | Sommer, Jr. et al. | 209/212 |
| 4,209,394 | 6/1980 | Kelland | 210/695 |
| 4,261,815 | 4/1981 | Kelland | 209/213 |
| 4,452,773 | 6/1984 | Molday | 424/1.37 |
| 4,526,681 | 7/1985 | Friedlaender et al. | 209/214 |
| 4,663,029 | 5/1987 | Kelland et al. | 209/214 |
| 4,664,796 | 5/1987 | Graham et al. | 210/222 |
| 4,795,698 | 1/1989 | Owen et al. | 435/4 |
| 4,869,811 | 9/1989 | Wolanski et al. | 209/212 |
| 4,946,590 | 8/1990 | Hertzog | 210/222 |
| 4,965,007 | 10/1990 | Yudelson | 252/62.53 |
| 5,186,827 | 2/1993 | Liberti et al. | 210/222 |
| 5,200,084 | 4/1993 | Liberti et al. | 210/695 |
| 5,466,574 | 11/1995 | Liberti et al. | 435/5 |

FOREIGN PATENT DOCUMENTS

| | | |
|---|---|---|
| WO9007380 | 7/1990 | WIPO. |
| WO9102811 | 3/1991 | WIPO. |
| WO91/09308 | 6/1991 | WIPO. |
| WO9411078 | 5/1994 | WIPO. |

OTHER PUBLICATIONS

H. Kolm et al., Scientific American, pp. 46–65 (Nov., 1975).
F. J. Friedlaender et al., IEEE Transactions on Magnetics, 15: 1526–1528 (1979).
F. J. Friedlaender et al., IEEE Transactions on Magnetics, 17: 2801–2803 (1981).
P.A. Liberti et al., Proceedings of the First John Ugelstad Conference, Apr. 8–9 (1991), ed. John Kemshed, pp. 47–56.

Primary Examiner—Marian C. Knode
Assistant Examiner—Susan C. Wolski
Attorney, Agent, or Firm—Dann, Dorfman, Herrell and Skillman

[57] ABSTRACT

Methods and devices are disclosed which are useful for collecting magnetic materials in either internally or externally generated magnetic gradient fields, followed by resuspension into solution with a simple manipulation of the magnetic device. The methods provide for removal of excess reagent, washing of magnetic material, and resuspension for analysis, among other uses. The methods are applicable to all types of biological material that are susceptible to magnetic labelling, including, for example, cells, viruses, proteins, hormones, and receptor-ligand complexes. Several devices are disclosed to take advantage of the method for cellular and immunoassay applications, including both internal and external devices. Both flow-through and static separators are disclosed.

25 Claims, 2 Drawing Sheets

METHODS AND DEVICES FOR MANIPULATION OF MAGNETICALLY COLLECTED MATERIAL

RELATED APPLICATIONS

This application is a continuation-in-part of U.S. patent application Ser. No. 08/228,818, filed Apr. 18, 1994, now U.S. Pat. No. 5,541,072, and of co-pending U.S. patent application Ser. No. 08/424,271, filed Apr. 24, 1995, which is a continuation-in-part of U.S. patent application Ser. No. 07/976,476, filed Nov. 16, 1992, now abandoned, which is a continuation-in-part of U.S. patent application Ser. No. 588,662, filed Sep. 26, 1990, now U.S. Pat. No. 5,200,084. The entire disclosure of each of the aforementioned patent and patent applications is incorporated by reference in the present specification as if set forth herein in full.

FIELD OF THE INVENTION

The present invention relates to a method for the magnetic collection of materials of interest with magnetic particles, and the subsequent controlled dispersion of the materials of interest. Several devices using this method of separation are disclosed. These devices include both internal and external magnetic gradients, as well as static and flow through-type separators. More specifically, biological substances such as cells, cell components, bacteria, viruses, toxins, nucleic acids, hormones, proteins, receptor-ligand complexes, other complex molecules or any combination thereof, can be first separated, and subsequently resuspended, while in the external magnetic field for further analysis, isolation or other use.

BACKGROUND OF THE INVENTION

A magnetic material or magnetic dipole will move in a magnetic field to the region of highest magnetic gradient. Magnetic gradients are broadly divided into two groups. Internal magnetic gradients are formed by inducing a magnetic field on some susceptible material placed in a magnetic field, giving rise to magnetic circuits which generate a gradient. Open field gradients are formed by magnetic circuits which exist around dipole magnets such as bar or horseshoe magnets or are formed by pole piece design, orientation or configuration. In the case of a simple rectangular bar magnet, field lines which form magnetic circuits conventionally move from North to South and are easily visualized with iron filings. From this familiar experiment in elementary physics it will be recalled that there is greater intensity of field lines nearest the poles. At the poles, the edges formed with the sides and faces of the bar will display an even greater density or gradient. Thus, a steel ball placed near a bar magnet is first attracted to the nearest pole and next moves to the region of highest gradient, typically the closest edge. For magnetic circuits any design which promotes increased or decreased density of field lines will generate a gradient. In opposing magnet designs, such as N-S-N-S quadrupole arrangements, opposing north poles or opposing south poles will have field lines which will not cross each other such that in the center of such an arrangement there will be zero field (no field lines crossing the center). From the circuits that result from North poles to each adjacent South pole such arrangements generate radial magnetic gradients.

Internal high gradient magnetic devices have been employed for nearly 50 years for removing weakly magnetic materials from slurries such as in the kaolin industry or for removing nanosized magnetic materials from solution. (See Kolm, Scientific American, Nov., 1975). Typically magnetic grade stainless steel wool is packed in a column which is then placed in a uniform magnetic field which induces gradients on the steel wool. See U.S. Pat. No. 3,676,337 to Kolm. Gradients as high as 200 kGauss/cm are easily achieved. The field gradient around a wire is inversely related to the wire diameter and the smaller the wire, the faster the gradient falls off. As will be described below, collection takes place on the wire surface when it is transverse to the external magnet field lines, but not when it is tangent to them. In using such a system, material to be separated is passed through the magnetic "filter" positioned in the external magnetic field. Next the material is washed and moved to a station outside the field where magnetic materials are removed, making the collector ready for reuse. Table I below indicates the strength of the magnetic gradient as a function of distance from ferromagnetic wires of diameters of 0.1 and 0.4 mm as calculated from Maxwell's equation. These are typical wire thicknesses for the devices described above. Note that the thinner wire has a higher gradient at the wire surface, but that the gradient drops off much more quickly.

TABLE I

| 0.1 mm diameter wire | | 0.4 mm diameter wire | |
|---|---|---|---|
| Distance from rod surface (mm) | Field Strength | Distance from rod surface (mm) | Field Strength |
| 0 mm (rod surface) | 170 KG/cm | 0 mm (rod surface) | 42.5 KG/cm |
| 0.05 mm | 21.1 KG/cm | 0.2 mm | 12.6 KG/cm |
| 0.10 mm | 6.3 KG/cm | 0.4 mm | 5.3 KG/cm |
| 0.15 mm | 2.7 KG/cm | 0.6 mm | 1.6 KG/cm |
| 0.20 mm | 1.4 KG cm | 0.8 mm | 0.6 KG/cm |

Various attempts have been made to perform continuous (non-cycle) high gradient magnetic separation. Improvements include flowthrough devices with fluctuating fields to separate the magnetic material from the non-magnetic. See U.S. Pat. No. 3,902,994 to Maxwell. Removable screens of ferromagnetic material are also well known in the art. See U.S. Pat. No. 4,209,394 to Kelland. In another device patented by Kelland, U.S. Pat. No. 4,261,815, the movement of magnetic materials from the low gradient to high gradient sides (hereafter referred to as quadrants) of wires positioned transverse to an external magnetic field was utilized to perform continuous separation of magnetic materials from tailings. The device incorporates a vertical flow chamber having wires placed therein parallel to the direction of flow. It is placed in an external magnetic field such that the field is perpendicular to the flow and wires therein. As can be visualized, magnetic material in such an arrangement will move from the low gradient sides of wires to the high gradient sides. As flow proceeds, the tailings will be unaffected by the magnetic gradient. Therefore, the high gradient quadrants will contain the original concentration of tailing and two times the original concentrations of magnetic material. After sufficient travel down the wires when separation has taken place, baffles can be positioned in a quadrant fashion to prevent the magnetic and non-magnetic quadrants from mixing and to allow collection of the appropriate quadrants. In theory this will result in either magnetically enriched or depleted feed stock. By rerunning the magnetically enriched fractions, another doubling of enrichment is achieved. Repetition of this process will result in relatively pure magnetic materials.

Another method of utilization of this same magnetic phenomenon was also devised by Kelland, et al, as described in U.S. Pat. No. 4,663,029. This patent teaches the use of a non-magnetic flow chamber adjacent at one side to a ferromagnetic rod or wire, which in the presence of a magnetic field will induce a magnetic gradient. Paramagnetic material will be attracted to the wire and diamagnetic material will be repelled from the wire, allowing collection of the magnetically unique material through ports either near or far from the wire. A similar gradation of materials by magnetic susceptibility was devised by Friedlaender, F. J., et al. and is the subject of U.S. Pat. No. 4,526,681.

A method of separation useful for cells and other fragile particles was described by Graham et al. in U.S. Pat. No. 4,664,796. This apparatus contains a rectangular chamber within a cylinder. One pair of opposing sides of the chamber are made of non-magnetic material, while the other set of opposing sides are made of magnetic material. This flow chamber is packed with a magnetically responsive interstitial separation matrix such as steel wool. The material to be separated is run through this chamber which is located in a homogeneous magnetic field. In the collection mode, the chamber is aligned in the external magnetic field such that the magnetic sides of the chamber are parallel with the magnets, thus inducing a high gradient field on the interstitial matrix in the chamber. When the chamber is in this position, magnetically labeled cells are attracted to the matrix and held, while the non-magnetic components are eluted. Upon rotation of the chamber, its magnetic sides will be perpendicular to the magnets, which will "shunt" or "short-circuit" the magnetic field, lowering the gradient in the flow chamber, and allowing the particles of interest to be removed by the shear forces of the fluid flow.

There are a variety of other internal magnetic devices whose gradient properties are used to achieve different applications. Commonly owned U.S. Pat. No. 5,200,084 teaches the use of thin ferromagnetic rods used to collect magnetically labeled cells from solution. Miltenyi (WO 90/07380) teaches the use of coated steel wool, or other magnetically susceptible material to separate cells. U.S. patent application Ser. No. 07/976,476, now abandoned by Liberti and Wang teaches an internal HGMS device useful for the immobilization of cells and subsequent sequential reactions of these cells. The teaching also allows for the observation of the immobilized cells. However, the resuspension and recovery of biological substances such as cells, which are either substantially undamaged or viable, remains a stumbling block that many recent patents have attempted to solve, but with only a limited degree of success.

External gradient magnetic configurations can also be used to collect magnetically responsive particles, particularly more magnetic ones. These external devices are so-named because there is no other component of the magnetic collector except the magnets or the pole pieces. These devices rely solely on the gradients that are created via the magnetic circuits generated by the quantity and placement of magnets and in some cases by imperfections of field lines moving through space. In a standard bar magnet, gradients exist because the magnetic field lines follow non-linear paths and "fan out" or bulge as they move from North to South. These effects create gradients of about 0.1 to 1.5 kGauss/cm in high quality laboratory magnets. These relatively low gradients can be increased by manipulating the magnetic circuits so as to compress or expand field line density. For example, if the gradient at one pole of a bar magnet is of insufficient strength, moving a second bar magnet with an identical field in opposition to the first magnet would cause repulsion between the two magnets. The number of field lines would remain the same, but they would become compressed as the two magnets were forced closer together. Thus, an increased gradient would result. The addition of magnets of opposing field to this dipole configuration to form a quadrupole could further increase the size of the region of high gradients. Other configurations such as adjacent magnets of opposing fields would also create gradients higher than those seen in a bar magnet of equivalent strength. Yet another method of increasing gradients in external field devices is by adapting the pole piece design. For example, if the configuration of a standard dipole magnet were changed by making one of the magnets into a pointed magnet, all field lines would flow towards the point, dramatically increasing the gradient around that region.

None of the effects described above are new. All have been described, used, and patented for use in various industries. For example, dipoles and quadrupoles have been used in the mining industry to separate clays and ores for decades. See U.S. Pat. No. 3,326,374 to Jones and U.S. Pat. No. 3,608,718 to Aubrey. Dipoles have also reportedly been used to prevent scale and lime build up in water systems. See U.S. Pat. No. 3,228,878 to Moody and U.S. Pat. No. 4,946,590 to Herzog. Adjacent magnets of opposing polarity have been used in drum or rotor separators for the separation of ferrous and non-ferrous pieces, such as those generated in scrap yards, an improvement over the use of electromagnets. See U.S. Pat. No. 4,869,811 to Wolanski et al. and U.S. Pat. No. 4,069,145 to Sommer et al.. Other pole piece designs are well known in the literature. See Liberti & Feeley, Proc of J.Ugelstad Conference, 1991.

External magnetic devices have also been used in the fields of cell separation and immunoassay. U.S. Pat. Nos. 3,970,518 and 4,018,886 to Giaever describe the use of small magnetic particles to separate cells using an actuating coil. Dynal Corp. (Oslo, Norway) exclusively uses simple external magnetic fields to separate the many particles which it markets for various types of cell separations. Commonly owned US patent applications Ser. Nos. 08/006,071, now U.S. Pat. No. 5,466,574, and 08/228,818, now U.S. Pat. No. 5,541,072, disclose the use of external fields to separate cells, manipulating the magnetic particles and collection devices to form monolayers of cells or other biological components. However, resuspension and recovery of collected materials still requires removal of the collection vessel from the gradient field and some level of physical agitation to accomplish this.

Turning now to the magnetic particles used in such collection devices, superparamagnetic materials have in the last 20 years become the backbone of magnetic separation technology in a variety of health care and bioprocessing applications. Such materials, regardless of their size (25 nm to 100 microns,) have the property that they are only magnetic when placed in a magnetic field. Once the field is removed, they cease to be magnetic and can normally easily be dispersed into suspension. The basis for superparamagnetic behavior is that such materials contain magnetic material in size units below 20–25 nm, which is estimated to be below the size of a magnetic domain. A magnetic domain is the smallest volume for a permanent magnetic dipole to exist. Hence, these materials are formed from one or more or an assembly of units incapable of holding a permanent magnetic dipole. The magnetic material of choice is magnetite, although other transition element oxides and mixtures thereof can be used.

Magnetic particles of the type described above have been used for various applications, particularly in health care, e.g.

immunoassay, cell separation and molecular biology. Particles ranging from 2 to 5 microns are available from Dynal. These particles are composed of spherical polymeric materials into which has been deposited magnetic crystals. These materials, because of their magnetite content and size, are readily separated in relatively low fields (0.5 to 2 kGauss/cm) which can easily be generated with open field gradients. Another similar class of materials are those particles of Rhone Poulanc which typically are produced in the 0.75 micron range. Because of their size, they separate more slowly than the Dynal beads in equivalent gradients. Another class of material is available from Advanced Magnetics. These particles are basically clusters of magnetite crystals, about 1 micron in size, which are coated with amino polymer silane to which bioreceptors can be coupled. These highly magnetic materials are easily separated in gradients as low as 0.5 kGauss/cm. Due to their size, both the Advanced Magnetics and Rhone Poulanc materials remain suspended for hours at a time.

There is a class of magnetic material which has been applied to bioseparations and which has characteristics that places this type of material in a special category. These are nanosized colloids (see, for example, U.S. Pat. Nos. 4,452,773 to Molday, 4,795,698 to Owen et al, 4,965,007 to Yudelson; and U.S. patent application Ser. No. 07/397,106 by Liberti, et al). They are typically composed of single to multicrystal agglomerates of magnetite coated with polymeric material which render them aqueous compatible. Individual crystals range in size from 8 to 15 nm. The coatings of these materials have sufficient interaction with aqueous solvent to keep them permanently in the colloidal state. Typically, well coated materials below 150 nm will show no evidence of settling for as long as 6 months and even longer. These materials have substantially all the properties of ferrofluids which might be referred to as their non-aqueous compatible cousins.

Because of their size and interaction with solvent water, substantial magnetic gradients are required to separate ferrofluids. It was customary in the literature to use steel wool column arrangements of the type described above which generate 100–200 kGauss/cm gradients. However, some years ago it was discovered that such materials must form "chains" in magnetic fields like beads on a string (markedly decreasing their Stokes' drag force) because separation can be achieved in gradient fields as low as 5 or 10 kGauss/cm. These discoveries lead to the development of devices using large gauge wires which generate relatively low gradients. Large gauge wires as well as other gradient surfaces can be used to cause ferrofluids to become deposited in a substantially uniform thickness upon collection. With the proper amounts of ferrofluid in a system, the thickness of the collected material is effectively the thickness of the magnetic colloid, meaning that a monolayer can be formed. Cells magnetically labeled can be made to easily form monolayers on macro wires or uniform gradient surfaces. See commonly owned U.S. Pat. No. 5,186,827 and U.S. patent application Ser. No. 08/006,071, now U.S. Pat. No. 5,466,574.

Many techniques used in biotechnology require processes such as identification, separation, and/or manipulation of target entities, such as cells or microbes, within a fluid medium such as bodily fluids, culture fluids or samples from the environment. It is also often desirable to maintain the target entity intact and/or viable upon separation or manipulation in order to analyze, identify, or characterize the target entities.

Identification techniques typically involve labeling the target entity with a reagent which can be detected according to a characteristic property. Entities which can be viewed optically such as cells or certain microbes, may be identified and/or characterized by using fluorescently labeled probes such as monoclonal antibodies or nucleic acids. Often the target of such probes is not accessible at the surface of the target entity or an excess of probe must be removed which requires washing steps and/or exposure to a variety of reagents facilitating the penetration of the probes. As the number of operations employed in such processes increases, a greater number of target entities are lost or no longer suitable for evaluation. Accurate microbial analyses employing such methodologies are difficult to achieve because of the small numbers of target entities involved, as well as the difficulty of washing away unbound labeling agent.

For example, to measure the absolute and relative number of cells in a specific subset of leukocytes in blood, a blood sample is drawn and. incubated with a fluorescently labeled antibody specific for this subset. The sample is then diluted with a lysing buffer, optionally including a fixative solution, and the dilute sample is analyzed by flow cytometry. This procedure for analysis can be applied to many different antigens. However, the drawbacks to this procedure become apparent when large samples are required for relatively rare event analyses. In those situations, the time needed for the flow cytometer to analyze these samples becomes extremely long, making the analysis no longer feasible due to economic constraints. In addition, intra-cytoplasmic and/or intra-nuclear analysis of cell content is difficult since multiple incubations and washing steps require prohibitively long processing times.

A particular nuisance that is often experienced when collection of magnetic materials is done with continuous flow-through devices is "piling-up" of the collected material on the inlet end of the device. This occurs because collection of magnetic material effectively extends the collection surface with collected material which in itself is magnetic. Thus collection distorts the surface and the concern over lack of uniformity of collection and of trapping of tailings become significant.

Another problem with continuous separation is that once the collector surface has filled to capacity with magnetically labeled material, the separator must be physically removed from the field or somehow demagnetized so as to remove magnetic material for subsequent reuse of the device.

SUMMARY OF THE INVENTION

A method of magnetic collection followed by magnetic resuspension is provided which takes advantage of the gradients which are generated in high gradient magnetic separation (HGMS). In practicing this invention, differences in the direction and magnitude of the gradients are exploited by employing methods which involve collection of magnetic material in one part of the gradient, then reversing the gradient direction to repel/resuspend the magnetic material. By employing an apparatus which is designed to move a ferromagnetic element between selected positions within the gradient, magnetically labelled materials are exposed first to a field which leads to the collection of the material on a surface associated with the ferromagnetic element, then to a field which acts to repel the material off that surface. This invention is particularly adaptable to the immobilization and manipulation of microscopic entities, including biological entities, such as cells. Methods are provided which enable both the separation of cells from fluid medium, as well as for their subsequent release as intact entities into the same or different fluid medium.

By operating in cycles which can involve filling of the collection chamber, magnetic collection, removal of tailings, washing, magnetic resuspension and harvesting of magnetic material, this invention obviates many of the above-noted problems encountered with traditional devices. Specifically, the present invention enables resuspension of collected, magnetically-labelled target substance in an efficient and reproducible manner so as to facilitate subjecting the target substances to detection or analysis systems, such as luminescence detectors, spectrophotometric analysis, fluorometers, flow cytometers, hematology analyzers, or other cell counting or analytical devices. This is achievable without the need for removing the magnetically-labelled target substance from the influence of the magnetic field, or for dislodging the collected target substance from its collection surface, followed by various forms of agitation such as stirring, shaking, vibration or mild sonication to resuspend the target substance. This cycling also allows the use of sequential reactions, which are important for the separation, labeling, and the manufacture of various substances, including the magnetic particles themselves.

According to one aspect of this invention, a method is provided for separating magnetic particles from a non-magnetic carrier medium containing the particles and dispersing the separated magnetic particles in a suitable dispersion medium, the carrier 10 medium and the dispersion medium being the same or different. The method initially involves providing in proximity to a separation chamber a ferromagnetic element, having a collection surface for the magnetic particles associated therewith and introducing the carrier fluid medium into the separation chamber.

A magnetic field is applied which intercepts the separation chamber, the magnetic field having a first region which exerts an attractive magnetic force urging magnetic particles in the carrier medium in a direction toward the ferromagnetic element and its associated collection surface and causing the magnetic particles to be collected on the surface, and a second region which exerts a repulsive force causing repulsion of the collected magnetic particles away from the ferromagnetic element and the collection surface, with the surface being movably positionable relative to said magnetic field.

The aforesaid surface is then positioned relative to the magnetic field for exposure to the first region and collection of magnetic particles attracted to the ferromagnetic element on the collection surface, and thereafter repositioned relative to the magnetic field for exposure to the second region, thereby repelling magnetic particles from the ferromagnetic element and dispersing the repelled particles in the dispersion medium.

According to another aspect of the present invention, there is provided an apparatus for separating magnetic particles from a non-magnetic fluid medium containing such particles. The apparatus comprises a housing, including an interior wall area, for receiving the fluid medium, and a ferromagnetic element, having a surface associated therewith, disposed in proximity to the housing.

A magnetic field source provides a magnetic field that intercepts the housing. The magnetic field has a first region which exerts an attractive magnetic force urging magnetic particles in the fluid medium in a direction toward the ferromagnetic element and the aforementioned surface, and a second region which exerts a repulsive force urging the magnetic particles away from the ferromagnetic element and the surface. The surface associated with the ferromagnetic element is movably positionable relative to the magnetic field so as to serve as a collection zone for collecting magnetic particles attracted to the element in a first position and to serve as a dispersion zone for dispersing magnetic particles repelled from the element in a second position.

The apparatus also includes means to move the surface selectively, such that in the first position the surface is in the first region and in the second position the surface is in the second region, and further includes barrier means in the housing, which comprises the surface associated with the ferromagnetic element and the interior wall area of the housing and which defines a chamber for confining the magnetic particles during movement of the surface from the first position to the second position.

When used for cellular analysis, the instant invention also makes possible a significant reduction in volume for all types of samples, resulting in higher concentrations of the target entity, thus permitting shorter analysis time. The ease of resuspension eliminates the need for centrifugation, a significant factor contributing to cell loss. The immobilization of cells permits many types of reactions to be performed which involve these cells.

When used for immunoassay, the instant invention provides a highly sensitive, but relatively small scale system for the collection of labeled analyte. The speed and reproducibility of collection and resuspension are important features for a relatively low-cost test for a multitude of different analytes. Further the resuspension principle is of significant benefit in constructing a reusable collection device making cleaning of the device an easier task as well.

DETAILED DESCRIPTION OF THE INVENTION

Figure 1:
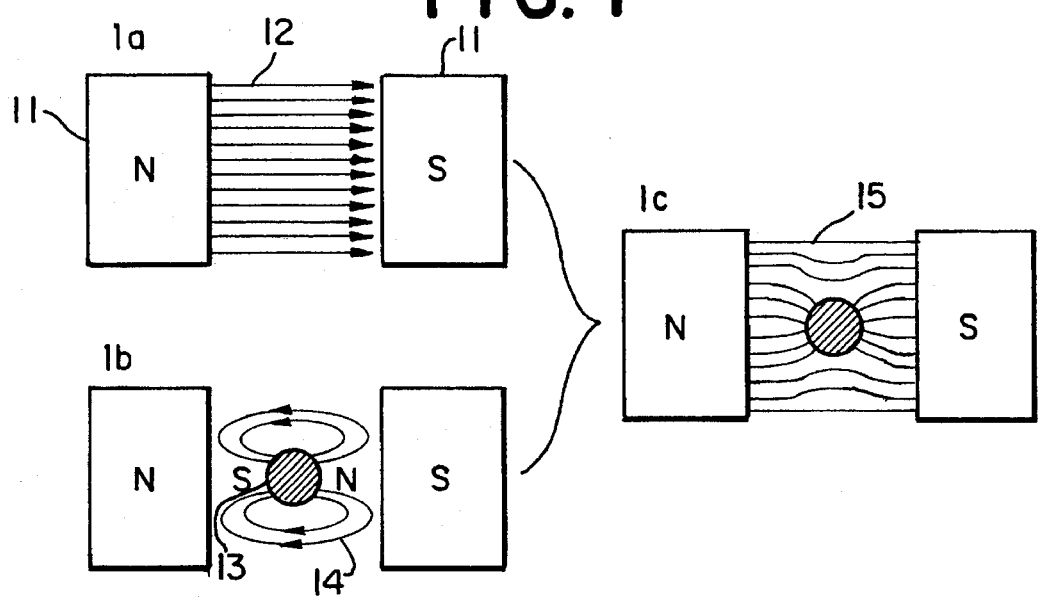
FIG. 1a depicts magnetic vectors in a uniform magnetic field.
FIG. 1b depicts the induced magnetic field lines generated by a ferromagnetic rod in the uniform field.
FIG. 1c depicts the vector addition of these two fields.

In the case of internal gradient magnetic devices a simple system to visualize is the cross-section of a single, typically round ferromagnetic element placed in a homogeneous magnetic field with the wire positioned transverse (perpendicular) to the field lines of the external field, as depicted in FIG. 1. FIG. 1a shows set of two opposed magnets 11, which form a magnetic field 12 between them. A ferromagnetic wire or rod 13 will have induced on it a magnetic dipole 14 by the external field 12, with its North pole facing the South pole face of the external field and similarly its South pole facing the external field North. The circuit that this induced magnet forms will be from its North to South poles and, as shown in FIG. 1b, these vector field lines on the surface of that part of the wire confronting the pole faces have the same direction as the external field lines, which will tend to increase the magnetic field in this area. However, on the surface of that part of the wire perpendicular to the pole faces of the magnets, the vector field lines have a direction opposite the external field lines, which will tend to decrease the magnetic field in this area. The net result of this vector addition/subtraction is field 15, depicted in FIG. 1c, in which there is augmentation of field lines on those areas of the wire surface facing the poles with a diminution of field lines on the other two areas.

Figure 2:
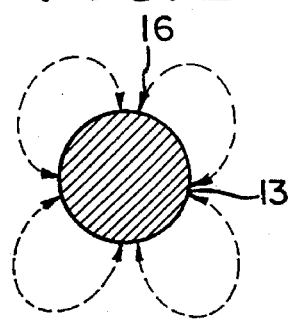
FIG. 2 depicts the trajectory that a magnetic entity follows if placed in the magnetic configuration of FIG. 1.

FIG. 2 is a schematic representation of the force exerted on a particle in field 15 (not shown) near the ferromagnetic rod 13. A magnetically responsive particle 16 located in the region of canceled magnetic field will tend to move towards a region of higher magnetic field, which in this case is initially away from rod 13. Then the force on the particle will turn the particle back towards the rod to the region of reinforced magnetic field. The region of highest field gradient is at the surface of the rod 13 facing the external magnets 11 (not shown). The vector lines indicate that magnetic materials placed on the lower gradient surfaces of the wire will move along the field lines to the higher gradient side. One can view the circumference around a wire as being divided into quadrants. The two quadrants facing the external pole faces function as collection surfaces, the other two being non-collection surfaces. This distinction is easy to demonstrate by observing the collection patterns with magnetic colloids. In experiments on suspensions of magnetically labeled mammalian cells placed in a microtitre well with a single wire traversing the well horizontally and positioned transverse to an external magnetic field, cells can microscopically be observed collecting on the sides of the wire facing the poles of the external field. Additionally, cells adjacent to the wire on the "low" gradient sides can be observed to move away from the wire and then circle back onto the "high" gradient sides. Thus the path that these cells actually follow is the vector lines depicted in FIG. 2.

Figure 3:
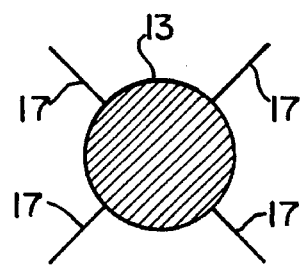
FIG. 3 is a schematic representation of the cross-section of a rod with baffles dividing the exterior of the rod into quadrants.
Figure 4:
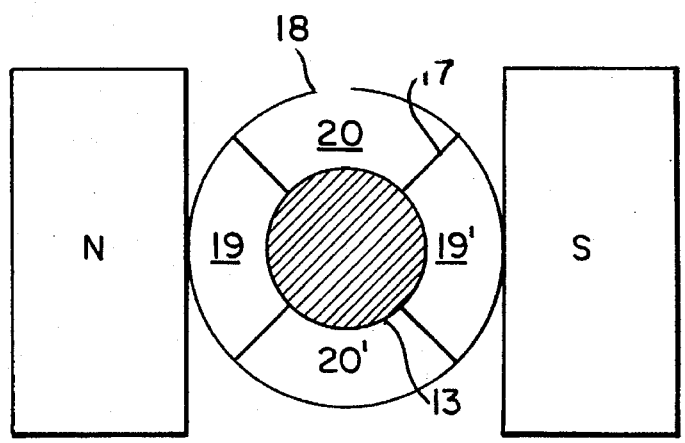
FIG. 4 depicts the apparatus of FIG. 3 inserted into a cylinder, which is further placed in a uniform magnetic field to form four separate regions which experience different magnetic forces.

Referring to FIGS. 3 and 4, the device shown is a ferromagnetic rod with four baffles or vanes, which will enable magnetic material to collect in chambers disposed on opposite sides of the rod. When the rod is turned 90 degrees, magnetic force will act to repel the collected material from the rod back into solution. This apparatus may be used in either a batch-type mode to separate relatively small quantities of material or with certain materials in a continuous flow mode to decrease the volume of the sample significantly by collecting material from a large volume on a surface and resuspending it in a small volume.

FIG. 3 shows the cross section of a ferromagnetic rod 13 of appropriate small diameter to generate a reasonably high gradient in a uniform magnetic field. The circumference of the wire or rod is sufficiently large that non-magnetic baffles 17 can be longitudinally attached to it, dividing the surface into four quadrants of approximately equal surface area.

As illustrated in FIG. 4, the rod 13 and baffles or vanes 17 are inserted into a cylinder 18 such that four distinct zones are formed. In three dimensions these zones are actually chambers. When this apparatus is in a uniform magnetic field it will be appreciated, by comparison with FIG. 2, that magnetic materials will be attracted to the surface of the ferromagnetic rod in the quadrants labeled 19 and 19'. The force lines which exist in quadrants 20 and 20' are directed away from the wire surface towards the inner wall of cylinder 18. Given these forces, a simple cyclic separation/resuspension system can easily be implemented. Magnetic feedstock or sample to be separated is fed into one or both of the chambers 19 and 19' and separation is allowed to take place. Next, those chambers can be emptied to collect the "tailing" if that is the objective, or the collected magnetic material may be washed by the addition of fresh wash liquid. With the chamber now refilled, by turning the rod 13 with its vanes 17 90°, material collected on the rod will be repelled from the rod surface and into solution. If need be, the material can be recollected and resuspended at will merely by sequentially turning the collection surface 90°. Optionally, the cylinder 18 can be moved as a single unit together with the rod and vanes. This apparatus should have inherently low non-specific binding to the collection device of material which is not magnetically labelled. Unlike most other internal gradient systems, there is little entrapment of particles due to the absence of steel wool mesh or other potentially entrapping arrangement of grids or wires. However, a coating on the wire may be necessary to reduce the oxidation of the apparatus over time. It should be apparent that the separation cycle could begin by filling the chamber in the non-collection mode.

Figure 5:
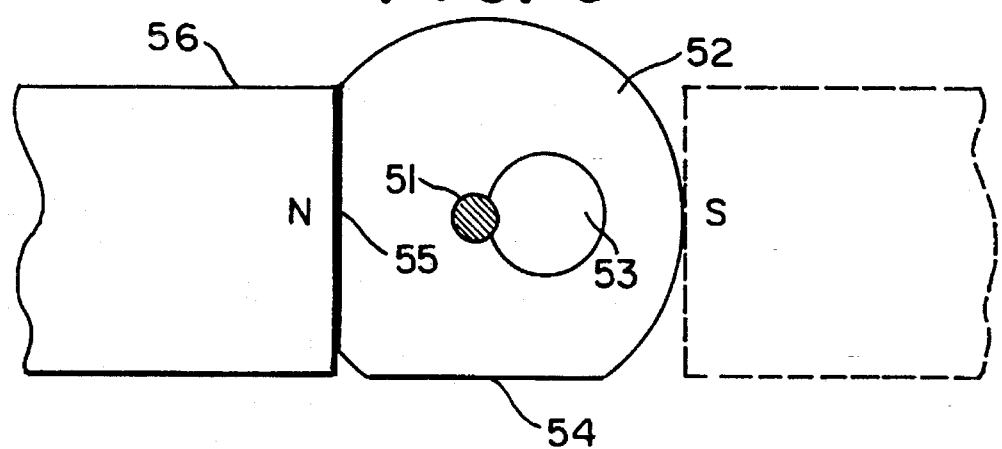
FIG. 5 depicts a cross section of an embodiment of the invention with a single collection chamber which can be alternated between two orientations adjacent to a magnet; one for magnetic collection, and one for magnetic resuspension.

In another embodiment of this invention, a single collection chamber 53 may be provided in a housing 52 as illustrated in FIG. 5. When side 55 of the housing is positioned adjacent to magnet 56, magnetically responsive material in chamber 53 will collect on the surface of the rod 51. However, if the device or the magnet is repositioned such that the magnet is adjacent to side 54 of the housing, any magnetic material on the surface of rod 51 will be repelled from the rod surface and be resuspended into any fluid present in chamber 53. The entire apparatus may be alternated between the collection and resuspension modes and a single chamber used to manipulate magnetically labeled cells or other target substances.

In yet another embodiment of the invention, one wall of the chamber need not be formed by a portion of the surface of the rod which generates the magnetic gradient. For example, a non-magnetic sleeve could be provided which surrounds and is substantially coextensive with the rod. The sleeve may be fabricated of a suitable biocompatible material for conducting biological separations, and provided with longitudinal vanes defining one or more separation chamber, as previously described. The sleeve may be affixed to, or rotatable relative to the ferromagnetic rod. In the latter embodiment, the chamber would be immediately adjacent to the rod, and either the rod or the chamber could be moved independently of one another. This would allow for removal of a disposable chamber, as may be necessary for some clinical applications. A removable rod might also be useful in some cases where variable field strengths (and thus variable wire diameters) might be desired.

It will be understood from the foregoing description that although the collection surface for the magnetic particles is associated with the ferromagnetic element, it may or may not be integral therewith. When the exterior of the ferromagnetic element and the collection surface are one and the same, or when the aforementioned sleeve is affixed to the ferromagnetic element, such that the collection surface of the sleeve and the ferromagnetic element are manipulatable as a unit, the structure is an integral or unitary whole.

It should be further understood that the rod or wire and associated collection chamber need not be placed in the homogeneous field generated between a pair of dipole magnets. Instead, the device could be placed adjacent to a magnetic field source which generates a sufficiently strong and homogeneous field to induce the appropriate gradient on the ferromagnetic element of such devices. A variety of such permanent or electromagnetic arrangements are known. Such an arrangement confers advantages not realized in a device sandwiched between two magnets. Namely, the field of collection need not be constrained to the side facing a magnet. In fact, with the proper materials engineering, a field of view can be established which leads to the complete exposure of the collected material to a viewing device. For example, in a very simple way, the device illustrated in FIG. 5 could be placed adjacent to a strong single magnet in a region where field lines are to the surface of the magnet facing the housing 52 and relatively homogeneous. If the device housing 52 were made out of clear glass, clear plastic, or quartz, optical or spectrophotometric devices could be used to observe or analyze the materials immobilized on the collecting rod. This embodiment of the invention provides for the reading or imaging of luminescent, absorptive, fluorescent, and/or light scattered signals.

Figure 6:
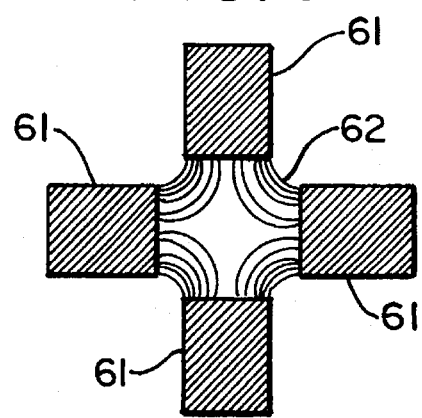
FIG. 6 depicts the magnetic field lines generated by a magnetic quadrupole.
Figure 7:
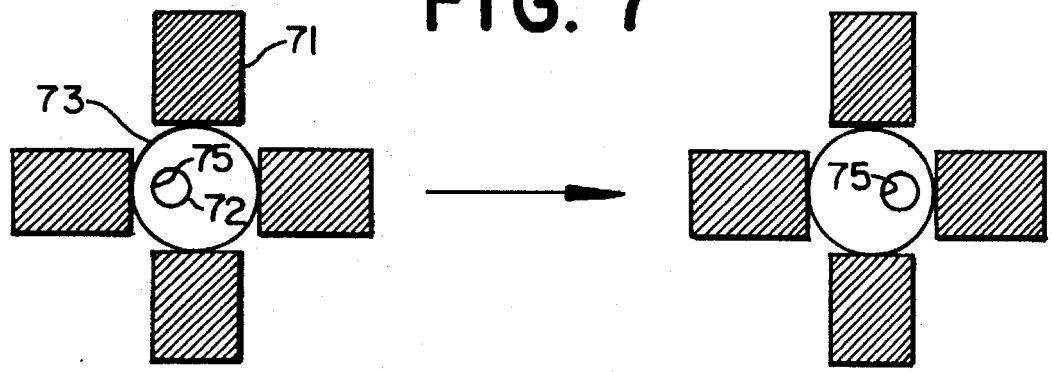
FIG. 7 is a schematic diagram of a magnetic separator which could be used in the two different configurations illustrated to expose material in the separator to different magnetic forces.

Referring to FIGS. 6 and 7, an apparatus is shown which employs a quadrupole magnet arrangement with a collection vessel located in the field such that the magnetic material collects on one side of the vessel. When the vessel is moved to a different region within the field of the quadrupole, the magnetic force will repel the magnetic material, and eventually it will collect again on another side of the vessel. However, before this second collection occurs, the material can be removed. This apparatus can also be used in either batch or continuous modes of operation.

The device of FIGS. 6 and 7 provides an alternative way of magnetically separating and resuspending material using the phenomenon of the magnetic force lines. This can be carried out by repositioning a collection chamber in magnetic gradients where gradient direction is reversed or altered. One way to achieve this objective is to employ the radial gradient generated in the quadrupole, or if less gradient is required, in a dipole arrangement. FIG. 6 also depicts the magnetic field lines 62 generated when magnets 61 are arrayed in a quadrupole arrangement. FIG. 7 depicts the manner in which separation may be effected by taking advantage of such force lines. A separation vessel 72 is placed in the radial field 62 (not shown) off center such that magnetic material is collected on the wall area 75 of vessel 72. By moving the vessel laterally to the region where wall area 75 experiences a magnetic gradient in the opposite direction as was previously the case, the magnetic material will resuspend. In time the magnetic material will recollect on the opposite wall of the tube. This apparatus can easily be used in either the batch or continuous mode. In batch mode operation, the collection vessel 72 could be a microtiter well for applications, such as immunoassay or a proportionally larger vessel and magnets, could be employed if needed for other applications. In continuous operation, the vessel would be provided with inlet/outlet ports at either end, which would be attached to tubing, through which the sample fluid could be flowed into the vessel. The non-magnetic components would be continuously removed through the opposite end. The vessel could be contained in a housing, which would control the placement of the vessel, allowing it to alternate between the two orientations within the field. It is also possible to simply place a piece of tubing through a quadrupole, securing it so that it remains fixed in place, and then moving the tubing or the magnets in relation to one another to resuspend the material.

The present invention provides methods and apparatus for efficiently determining a broad range of target substances or analytes. In a preferred embodiment, the methods and devices of the invention are used for the determination of any constituent of a biological fluid or specimen that is capable of selective interaction with a specific binding substance. Thus, the term "target substance" as used herein, refers to a wide variety of substances of biological or medical interest which are measurable individually or as a group. Examples include cells, both eucaryotic (e.g., leukocytes, erythrocytes or fungi) and procaryotic (e.g., bacteria, protozoa or mycoplasma), viruses, cell components, molecules (e.g., proteins) and macromolecules (e.g., nucleic acids-RNA, DNA). These substances may be determined as discrete entities or in the form of complexes or aggregates. Such determinations are accomplished using certain methods of the invention which rely on the selective interaction of the specific binding substance with at least one characteristic determinant of the target substance or analyte of interest.

The term "determinant" is used herein in its broad sense to denote an element that identifies or determines the nature of something. When used in reference to any of the foregoing target substances, "determinant" means that portion of the target substance involved in and responsible for selective binding to the specific binding substance, the presence of which is required for selective binding to occur. Cell-associated determinants include, for example, components of the cell membrane, cytoplasm or nucleus. Among such cell-associated structures are membrane-bound proteins or glycoproteins, including cell surface antigens of either host cell or viral origin, histocompatibility antigens, or membrane receptors. One class of specific binding substance that is used to selectively interact with the determinants is the class of antibodies capable of immunospecifically recognizing same. The term "antibody" as used herein includes immunoglobulins, monoclonal or polyclonal and immunoreactive immunoglobulin fragments.

Further examples of characteristic determinants and their specific binding substances are: receptor-hormone, receptor-ligand, agonist-antagonist, RNA or DNA oligomers-complimentary sequences, Fc receptor of mouse IgG-protein A, avidin-biotin and virus-receptor. Still other determinant-specific binding pair combinations that may be determined using the methods of this invention will be apparent to those skilled in the art.

The preferred magnetic particles for use in carrying out this invention are particles that behave as true colloids. Such particles are characterized by their sub-micron particle size, which is generally less than about 200 nanometers (nm) (0.20 microns), and their stability to gravitational separation from solution for extended periods of time. Such small particles facilitate observation of the target entities via optical microscopy since the particles are significantly smaller than the wavelength range of light. Suitable materials are composed of a crystalline core of superparamagnetic material surrounded by molecules which may be physically absorbed or covalently attached to the magnetic core and which confer stability to the colloidal particles. The size of the colloidal particles is sufficiently small that they do not contain a complete magnetic domain, and their Brownian energy exceeds their magnetic moment. As a consequence, North Pole, South Pole alignment and subsequent mutual attraction/repulsion of these colloidal magnetic particles does not appear to occur even in moderately strong magnetic fields, contributing to their solution stability. Accordingly, colloidal magnetic particles are not readily separable from solution as such even with powerful electromagnets, but instead require a magnetic gradient to be generated within the test medium in which the particles are suspended in order to achieve separation of the discrete particles.

Magnetic particles having the above-described properties can be prepared as described in U.S. Pat. No. 4,795,698, and U.S. patent application Ser. No. 07/397,106, the entire disclosures of which are incorporated by reference in the present specification, as if set forth herein in full.

For immobilization of cellular target entities, for example, the test medium typically comprises appropriately prepared fluids, for example, body fluids such as blood, urine, sputum or secretions. It is preferable to add the colloidal magnetic particles to the test medium in a buffer solution. A suitable buffer solution for this purpose comprises a mixture of 5% bovine serum albumin ("BSA") and 95% of a biocompatible phosphate salt solution, optionally including relatively minor amounts of dextrose, sodium chloride and potassium chloride. The buffer solution should be isotonic, with a pH about 7. The protein serves to decrease interactions which tend to interfere with the analysis. The target substance may be added to the test medium before, after or simultaneously with introduction of the magnetic particles. The practice of this invention takes advantage of the diffusion controlled solution kinetics of the colloidal magnetic particles, which may be further enhanced by the addition of heat to the test medium. The test medium is usually incubated to promote binding between the receptor and any ligand of interest present therein. Incubation is typically conducted at room temperature or at a temperature slightly above the freezing point of the test medium (i.e., 4° C. in an aqueous medium). The period of incubation is normally of short duration (i.e., about 15 minutes). The test medium may be agitated or stirred during the incubation period to facilitate contact between receptors and ligands.

The invention disclosed here can be utilized in conjunction with the invention disclosed in U.S. patent application Ser. No. 08/228,818, now U.S. Pat. No. 5,541,072 to achieve performance in relatively low gradient fields, as would be the case for relatively large diameter ferromagnetic collection rods. In the last-mentioned patent application, it is disclosed that a certain class of magnetic material, referred to as ferrofluids, form phases with non-ferrofluid solutions. For example when a dilute solution of aqueous soluble ferrofluid (see commonly owned US patent application Ser. No. 07/397,106) is layered onto the aqueous solvent of the ferrofluid, the ferrofluid solution will fall below the solvent and form two phases which will remain distinct. Further, these phases will be magnetically responsive. Thus if two phases, each 2 cm high, are formed in a 10×75 mm test tube, the ferrofluid phase being the bottom phase, and a bar magnet is brought to the side of the tube, the phases will reorient themselves vertically in the tube with the ferrofluid phase being closest to the magnet. Similarly, if the tube were placed in a radial gradient magnetic field, the ferrofluid would form an annular ring with an inner cylinder of solvent alone. This phasing phenomena can be used, as already disclosed, to position material which is to be separated substantially uniformly along a gradient surface and in closer proximity to the region of highest gradient than would be the case without phasing. This proximity of magnetic material to the region of highest gradient leads to more rapid and uniform separation. The ability to use the device and method described herein in conjunction with the ferrophasing phenomenon broadens the application possibilities of this invention. For example, to isolate infrequent cells, which are defined here as cells that occur at a frequency below one in $10^2$, Such as circulating malignant cells, fetal cells, progenitor cells, basophils, or eosinophils, this invention can be used in the flow through mode described above. Rare cells can be labeled with antibody and a magnetic ferrofluid capable of exhibiting the ferrophasing behavior. If the apparatus described above and illustrated in FIGS. 4 or 5 were filled with a non-magnetic buffer, then when the magnetically labeled cell sample is flowed into the apparatus, the ferrophasing phenomenon would cause submergence of the labelled sample through the non-magnetic buffer to the region adjacent to the rod along substantially the entire length thereof. This region is the region of the highest magnetic gradient, so that any magnetically labelled cells would be almost immediately captured. At the surface of the rod, the magnetic gradient would be sufficiently high to destroy the ferrophase, causing it to separate into magnetic and non-magnetic components. The non-magnetic material, including non-labeled cells would diffuse into the non-magnetic buffer, being carried out of the apparatus with the fluid flow.

A further beneficial effect of the ferrophasing phenomenon is the resultant distribution of the magnetically collected cells along substantially the entire length of the rod, avoiding the effect the of "piling up" at the inlet, as seen in many HGMS systems. After the entire sample has been flowed into the magnetic collector, buffer could be used to remove the remaining non-magnetic material, and the apparatus could be rotated 90° with respect to the magnetic field. The magnetically labeled cells would then be resuspended and flowed out of the magnetic collector. It is important to note that this method of operation allows for a significant reduction in the volume of a sample. A relatively large volume of sample can be flowed through the system, with an extremely low incidence of rare cell events. Then after a short residence time in the apparatus, a significantly enriched cell population can be released in a small volume.

The entire disclosure of the aforementioned U.S. patent application Ser. No. 08/228,818, now U.S. Pat. No. 5,541,072, is incorporated in the present specification by reference as if set forth herein in full.

The advantages conferred by the instant invention over the state of the art are many. Devices such as those described above allow for relatively easy magnetic collection, resuspension, and if desired, the process can be repeated. In applications relating to cellular biology, the present invention obviates the need to perform multiple centrifugations for washing out unbound reagents. This is a tremendous advantage over the current art, eliminating the cell loss and clumping that often results from centrifugation. In applications relating to immunoassay, the ease of complete resuspension of labeled analyte without clumping is vital to reproducible analysis of analytes such as TSH, T4, hCG, etc. This advantage is also important in applications other than cellular biology or immunoassay. The ability to carry out resuspension in the separation chamber affords other advantages as labeled material can then be removed from the chamber for analysis elsewhere, such as to read a signal from the collected material, to measure the amount of collected material, to count the number of cells, etc. In addition, many types of reactions may be facilitated by collection of the magnetically labeled material, and washing out of the excess reactant. Examples include enzymatic reactions, labelling reactions, hybridization reactions, protein binding reactions, immunochemical reactions, which can be either single step or multi-step reactions. Such reactions can be performed with the target substance in the magnetically immobilized state where reactants can be removed by flowing them out of the chamber. This process not only provides for efficiency, but also for economy of reagents. The present invention also enables the performance of various analyses while the target substance is immobilized.

Applications for this method of magnetic manipulation are many. In the field of diagnostic medicine, a blood sample could be incubated with fluorescently labeled antibodies identifying subsets of leukocytes and magnetically labeled monoclonal antibodies which recognize all leukocytes. The leukocytes may be magnetically removed from a blood sample and non-targeted cells (red blood cells and platelets) could be washed out of the system. The leukocytes, which may be collected as a monolayer, could be exposed to a variety of reagents, while immobilized on the collection surface. The ability to immobilize target cells permits the implementation of procedures such as in-situ hybridization (ISH), in-situ PCR, or functional assays. In the field of therapeutic medicine, genetically manipulated cells may be isolated from non-manipulated cells by the presence of a surface marker. In the field of food testing, pathogens present on carcasses or other surfaces could be analyzed for antibiotic susceptibility or pathogenicity. In the field of macromolecule separation such as immunoassays or molecular biology, the ability to resuspend magnetically collected materials could have many benefits, such as the ability to hybridize, do sequential reactions or protein/enzyme incubations in solution, while easily separating the desired material after the reactions in solution have occurred. Alternately, some reactions that have been practically impossible to do, become possible with such tight control over separation and resuspension. For example, it should be possible to do intracellular immunoassays, for example for HIV or carcinoembryonic antigen (CEA). In an intracellular immunoassay, the cell membrane could be permeabilized, then a reactant allowed to infuse the cell. Functional studies on cells could also be accomplished with the instant invention. A virus, bacteria, chemical agent, drug, or other biological molecule could be introduced to some cells immobilized in a collection chamber for a brief period, after which the buffer containing the pathogen or agent could be easily washed out. Then the effect of the pathogen or agent on the cell could be observed. Any effects would be solely due to the introduced material. For example, the cells could be exposed to foreign antigens or ligands and subsequently analyzed for intracellular phosphorylation of proteins involved in the activation pathways of the stimuli. This could lead to easier toxicity testing, disease resistance testing or cell function testing.

Many different types of devices using this method of manipulation could be manufactured. The two internal rod devices and the external well/flow-though device that are illustrated in FIGS. 3-7 are some examples. However, this type of magnetic collection system need not stand alone in a clinical or laboratory situation. This type of device could be used as a front-end unit for cell analysis systems such as hematology analyzers or flow cytometers. For example, this device could be used with whole blood to collect leukocytes, obviating the need to gradient centrifuge whole blood to isolate mononuclear cells or erythrocyte lysed blood.

Another application of the device of the instant invention involves use as an analysis chamber. A chamber could be constructed with a collection surface visible to some means of detection, such as fluorescent, chemiluminescent, spectrophotometric, or visual. The desired substance could be labeled with magnetic material and collected on the surface, preferably in a monolayer or approximately a monolayer. Optionally, the material could be subjected to any of the reactions or manipulations described previously. Then, the material could be observed, detected, measured, counted or otherwise quantified while the material remains immobilized in the device.

The present invention also provides a device in which the housing moves independently of the rod. This type of housing could have two chambers, which have a different volume, and which are connected, but which also include a barrier that separates the two chambers. With the barrier closed, the larger chamber could be filled with material to be separated, which material is then collected on the rod. Then, with the barrier open, the housing could be rotated around the rod, not disturbing the cells immobilized on the rod such that the cells are encased within the smaller chamber. The barrier between the two chambers could then be closed. Since the second chamber has a volume smaller than the first chamber, this manipulation allows for resuspension in a smaller volume.

Another aspect of the present invention involves the construction of a ferromagnetic probe which may be lowered into a vessel such as a microtiter well placed in a uniform magnetic field. In one orientation, the probe would collect magnetically responsive material. After a rotation of the probe 90°, the material collected would be dispersed. Thus, magnetic material could be removed from a first vessel and redispersed in a second vessel for washing or subsequent detection. One embodiment would resemble a small probe with a ferromagnetic segment having two opposing quadrants blocked to magnetic collection, covering approximately half of the ferromagnetic segment of the probe. The probe could be inserted into a microtiter well or other chamber with a sample containing an analyte of interest and placed in a uniform magnetic field. Magnetically labelled analyte would be collected upon the probe. The probe could optionally be washed, then turned 90° for resuspension into an analysis solution, optionally containing substrate for chemiluminescent or other detection. Numerous other devices can be envisioned which exploit this method of magnetic separation, in addition to those described and exemplified herein.

This method of magnetic separation and resuspension is especially adaptable to analysis of individual events, such as will be the case in the next several generations of particle analyzers. Devices for implementing the methods of the present invention are suitable for microfabrication, to separate very small samples of material, on the scale of microliters. The present invention may also be utilized as a front-end system of separation which could handle quantities of blood or other samples anywhere in the microliter to liter range.

The following examples will serve to illustrate the principles of this invention; however, these examples should not be construed as limiting the scope of this invention.

EXAMPLE 1

Internal Collection Device for

Resuspendable Magnetic Collection

The fabrication of the embodiment of the invention illustrated in FIG. 5 will now be described.

A ferromagnetic element was manufactured (Jade, Huntingdon Valley, Pa.) out of soft metal iron rod with a radius of 1.0 mm and a length of 10 cm. A single collection chamber of a radius of 1.53 mm was formed in a solid acrylic body in the shape of a truncated cylinder which served as the housing around the rod. The collection chamber was parallel to the rod, and its circumference overlapped that of the rod, as shown in FIG. 5. Gradient field strength at the surface of the rod was approximately .5 kGauss/cm, and the volume of the chamber was approximately 650 μl.

To demonstrate magnetic collection and resuspension, magnetically responsive particles coated with bovine serum albumin (BSA) were manufactured as disclosed in U.S. patent application Ser. No. 07/397,106. The particles were of a size approximately 100 nm diameter. The collection chamber was filled with this BSA ferrofluid at a concentration of 50 ug iron/ml in 20 mM sodium phosphate buffer at pH 7.2. The device was positioned horizontally into a yoked permanent magnet fixture having 5×10 cm pole faces and a 1 cm gap near the midline of the pole faces. The yoke fixture positions two 5×10×2 cm rare earth magnets such that the pole face planes are vertical, the 10 cm dimension is horizontal and the gap opening is at the top and sides which allows easy insertion and viewing of the device. In the horizontal region near the center of the pole faces the field for this fixture was 7.5 kGauss and very homogeneous. By first inserting the ferrofluid filled collection/resuspension device into the magnetic field such that its orientation with respect to the field put the device in the "resuspension" mode, it could be determined visually that no collection occurred, nor was any other change visible. Next the device was rotated 90° to the collection orientation, i.e., the position shown in FIG. 5, and collection of the ferrofluid on the ferromagnetic rod was observed. The device was then rotated back to its original orientation and the ferrofluid was observed to resuspend. This cycle of collection and resuspension was repeated several times. Additionally the device was removed from the magnetic field in the resuspension mode and the device emptied. The ferrofluid was observed to be fully resuspended and non aggregated.

EXAMPLE 2

The Effect of Ferrophasing

To demonstrate the ferrophasing phenomenon two experiments were done. Holding the chamber in a vertical position it was half filled with ferrofluid at 50 ug iron/ml in phosphate buffer. Next buffer was layered onto the ferrofluid so that no bubbles remained in the chamber. The device in the same vertical position was carefully lowered into the magnetic field in the non-collection orientation until that portion containing the ferrofluid was completely in the field. At that point the device was rotated to the horizontal position and observed. The ferrofluid and buffer solution remained on their respective ends of the chamber. Next the device was rotated into the collection orientation whereupon the ferrofluid solution could be observed to immediately move under the buffer forming a uniform layer along the entire length of the collection rod.

In a related experiment the device was filled with buffer placed in the magnetic field in the collection orientation and a small quantity of ferrofluid solution (approximately 20% of the chamber volume) was injected into the chamber. Immediately upon entry of the ferrofluid into the chamber it moved along the entire length of the collection rod forming a uniform phase which subsequently collected.

While certain preferred embodiments of the present invention have been described and exemplified above, it is not intended to limit the invention to such embodiments, but various modifications may be made thereto, without departing from the scope and spirit of the present invention as set forth in the following claims.

What is claimed is:

1. A method for separating magnetic particles from a non-magnetic carrier medium containing said particles and dispersing said separated magnetic particles in a dispersion medium, said carrier medium and said dispersion medium being the same or different, said method comprising:

introducing said carrier medium into a separation chamber;

providing a ferromagnetic element either in or adjacent to said separation chamber, and a collection surface, wherein said collection surface is selected from the group consisting of a wall of said separation chamber, a portion of said ferromagnetic element and a wall of a collection chamber disposed in said separation chamber;

applying a magnetic field which intercepts said separation chamber, said magnetic field having a first region which exerts an attractive magnetic force urging magnetic particles in said carrier medium in a direction toward said ferromagnetic element and said surface and causing said magnetic particles to be collected on said surface, and a second region which exerts a repulsive force causing repulsion of said collected magnetic particles away from said ferromagnetic element and said surface, said surface being movably positionable relative to said magnetic field;

positioning said surface relative to said magnetic field for exposure to said first region and collecting on said surface said magnetic particles attracted to said element; and repositioning said surface relative to said magnetic field for exposure to said second region and dispersing said magnetic particles repelled from said element in said dispersion medium.

2. A method according to claim 1 which further comprises providing an enclosure for said surface and confining said magnetic particles within said enclosure during positioning and repositioning of said surface.

3. A method for separating a target substance having at least one characteristic determinant from a fluid medium suspected of containing said target substance, said method comprising:

a. contacting said fluid medium with a quantity of magnetic particles having directly or indirectly immobilized on their surface a specific binding substance that binds specifically to said at least one characteristic determinant, under conditions causing binding of said at least one characteristic determinant to said specific binding substance, resulting in target substance-bearing magnetic particles;

b. introducing said fluid medium into a separation chamber;

c. providing a ferromagnetic element either in or adjacent to said separation chamber, and a collection surface, wherein said collection surface is selected from the group consisting of a wall of said separation chamber, a portion of said ferromagnetic element, and a wall of a collection chamber disposed in said separation chamber;

d. applying a magnetic field which intercepts said separation chamber, said magnetic field having a first region which exerts an attractive magnetic force urging said target substance-bearing magnetic particles in said fluid medium in a direction toward said ferromagnetic element and said surface and causing said target substance-bearing magnetic particles to be collected on said surface, and a second region which exerts a repulsive force causing repulsion of said collected target substance-bearing magnetic particles away from said ferromagnetic element and said surface, said surface being movably positionable relative to said magnetic field;

e. positioning said surface relative to said magnetic field for exposure to said first region and collecting on said surface said target substance-bearing magnetic particles attracted to said element;

f. discharging said fluid medium from said separation chamber;

g. introducing dispersion medium into said separation chamber;

h. repositioning said surface relative to said magnetic field for exposure to said second region and dispersing said target substance-bearing magnetic particles repelled from said element in said dispersion medium; and i. recovering said target substance-bearing magnetic particles.

4. A method as claimed in claim 3, wherein the steps of discharging said fluid medium from, and introducing dispersion medium into said separation chamber are performed substantially simultaneously.

5. A method as claimed in claim 3 including the step of causing said target substance to undergo a reaction with a reactant while said target substance-bearing magnetic particles are collected on said surface.

6. A method as claimed in claim 5, wherein said reaction is an immunochemical reaction in which an immunochemical reactant is caused to bind specifically to said at least one characteristic determinant of said target substance.

7. A method as claimed in claim 6, wherein said immunochemical reactant is an antibody.

8. A method as claimed in claim 5, wherein said reaction is a labeling reaction in which a labeling reactant is caused to react with said target substance.

9. A method as claimed in claim 8, wherein said labeling reactant immunochemically reacts with said target substance.

10. A method as claimed in claim 9, wherein said labeling reaction comprises labeling said target substance with a labeling reactant comprising a detectable label which is directly or indirectly conjugated to a specific binding substance which specifically binds to said at least one said characteristic determinant of said target substance.

11. A method as claimed in claim 9, wherein said labeling reaction comprises sequentially binding to said target substance a first specific binding substance that specifically binds to at least one characteristic determinant of said target substance and a labeling reactant comprising a detectable label which is directly or indirectly conjugated to a second specific binding substance which specifically binds to said first specific binding substance.

12. A method as claimed in claim 3, which further includes, after discharging said fluid medium from, and before introducing dispersion medium into said separation chamber, introducing a wash liquid into said separation chamber with said target substance-bearing magnetic particles collected on said surface, exposing said surface to said second region thereby dispersing said target substance-bearing magnetic particles in said wash liquid, recollecting said target substance-bearing magnetic particles on said surface and removing said wash liquid from said separation chamber.

13. A method as claimed in claim 3, including the step of subjecting said target substance to analysis while said target substance-bearing magnetic particles are collected on said surface.

14. A method as claimed in claim 13, wherein said target substance is a biological substance selected from the group consisting of cells, cell components, bacteria, viruses, toxins, nucleic acids, hormones, proteins, receptor-ligand complexes, and any combination thereof.

15. Apparatus for separating magnetic particles from a non-magnetic fluid medium containing said particles, said apparatus comprising:

a housing for receiving said fluid medium, said housing having an interior wall area;

a ferromagnetic element disposed either in or adjacent to said housing;

a collection surface, wherein said collection surface is selected from the group consisting of a wall of said housing, a portion of said ferromagnetic element, and a wall of a collection chamber disposed in said housing;

a magnetic field source providing a magnetic field which intercepts said housing, said magnetic field having a first region which exerts an attractive magnetic force urging magnetic particles in said fluid medium in a direction toward said ferromagnetic element and said surface, and a second region which exerts a repulsive force urging said magnetic particles away from said ferromagnetic element and said surface, said surface being movably positionable relative to said magnetic field to serve as a collection zone for collecting magnetic particles attracted to said element in a first position and to serve as a dispersion zone for dispersing magnetic particles repelled from said element in a second position;

means to move said surface selectively, in said first position and said surface being in said first region and in said second position said surface being in said second region; and a chamber in said housing for confining said magnetic particles during movement of said surface from said first position to said second position, wherein said chamber comprises either said collection chamber disposed in said housing or a chamber defined by at least said surface and an interior wall area of said housing.

16. Apparatus as claimed in claim 15, wherein said housing has a longitudinal axis and said ferromagnetic element is an elongate rod having a centerline oriented along the longitudinal axis of said housing.

17. Apparatus as claimed in claim 16, wherein said magnetic field source comprises a pair of pole pieces each said pole piece having a face confronting the face of the other pole piece for generating magnetic flux lines extending between pole pieces transverse to the longitudinal axis of said housing, the centerline of said ferromagnetic element being substantially perpendicular to said magnetic flux lines.

18. Apparatus as claimed in claim 17, including a non-magnetic sleeve having an external wall surface, said sleeve surrounding and being substantially coextensive with said elongate rod.

19. Apparatus as claimed in claim 18, wherein said sleeve is rotatably movable relative to said elongate rod.

20. Apparatus as claimed in claim 19, wherein said sleeve includes at least two non-magnetic vanes longitudinally disposed at spaced apart locations on said external wall surface, and wherein said vanes, the external wall surface of said sleeve between said vanes, and said interior wall area of said housing define said chamber.

21. Apparatus as claimed in claim 16, wherein said elongate rod is cylindrical with a diameter in the range of 0.05–4.0 mm.

22. Apparatus as claimed in claim 16 having an inlet opening for receiving said fluid medium and an outlet opening for discharging said fluid medium, said inlet opening and said outlet opening being disposed at opposite ends of said housing.

23. Apparatus as claimed in claim 16, including an impeller for inducing flow of said fluid medium through said housing.

24. Apparatus as claimed in claim 23, wherein said impeller is a pump.

25. Apparatus as claimed in claim 15, wherein said surface is a portion of said ferromagnetic element.

* * * * *